(12) United States Patent
Deshmukh

(10) Patent No.: US 10,481,055 B2
(45) Date of Patent: Nov. 19, 2019

(54) SYSTEM AND METHOD FOR REFILLING CRYOGEN IN MICROSCOPE CRYOGEN HOLDERS

(71) Applicant: Simple Origin, Inc., Pittsburgh, PA (US)

(72) Inventor: Pushkarraj Deshmukh, Pittsburgh, PA (US)

(73) Assignee: Simple Origin, Inc., Pittsburgh, PA (US)

( * ) Notice: Subject to any disclaimer, the term of this patent is extended or adjusted under 35 U.S.C. 154(b) by 197 days.

(21) Appl. No.: 15/671,711

(22) Filed: Aug. 8, 2017

(65) Prior Publication Data
US 2018/0058990 A1  Mar. 1, 2018

Related U.S. Application Data

(60) Provisional application No. 62/379,838, filed on Aug. 26, 2016.

(51) Int. Cl.
*F17C 7/02* (2006.01)
*F17C 5/02* (2006.01)
*F17C 13/04* (2006.01)
*F25D 3/10* (2006.01)
*F25B 19/00* (2006.01)
(Continued)

(52) U.S. Cl.
CPC ............. *G01N 1/42* (2013.01); *F25D 3/10* (2013.01); *G01F 23/0076* (2013.01); *G01F 23/246* (2013.01); *G01F 23/296* (2013.01); *H01J 37/26* (2013.01); *F25D 2400/30* (2013.01); *H01J 2237/002* (2013.01); *H01J 2237/022* (2013.01); *H01J 2237/028* (2013.01); *H01J 2237/2001* (2013.01)

(58) Field of Classification Search
CPC ...... F17C 5/02; F17C 6/00; F17C 2250/0408; F17C 2250/0439; F17C 13/04; F17C 7/02; F25D 3/10; F25D 3/102; F25D 3/105; F25B 19/00
See application file for complete search history.

(56) References Cited

U.S. PATENT DOCUMENTS 2,970,604 A * 2/1961 Henry ................ F17C 13/02
  137/206
3,195,620 A * 7/1965 Steinhardt, Jr. ......... F17C 3/085
  165/104.14
(Continued)

*Primary Examiner* — Frantz F Jules
*Assistant Examiner* — Erik Mendoza-Wilkenfel
(74) *Attorney, Agent, or Firm* — Fox Rothschild LLP

(57) ABSTRACT

A cryogen refilling system includes a reservoir assembly for holding cryogen and a delivery channel in fluid communication with the reservoir assembly for delivering cryogen from the reservoir assembly to a microscope cryogen holder. The delivery channel includes at least one control valve. The system also includes a sensor-lid assembly and a controller. The sensor-lid assembly includes a sensor assembly configured to detect a level of cryogen in the microscope cryogen holder. The controller is configured to receive sensor data from the sensor assembly, analyze the sensor data to determine whether the microscope cryogen holder requires refilling, and in response to determining that the microscope cryogen holder requires refilling, cause a valve control mechanism to open the at least one control valve of the delivery channel.

52 Claims, 6 Drawing Sheets

(51) Int. Cl.
  *G01N 1/42*  (2006.01)
  *G01F 23/296*  (2006.01)
  *H01J 37/26*  (2006.01)
  *G01F 23/00*  (2006.01)
  *G01F 23/24*  (2006.01)

(56) References Cited

U.S. PATENT DOCUMENTS

| | | | | |
|---|---|---|---|---|
| 4,827,762 | A | * | 5/1989 | Hasselmann ............ G01F 1/007 702/51 |
| 5,419,140 | A | * | 5/1995 | Germain .................... F25D 3/10 62/375 |
| 2004/0045315 | A1 | * | 3/2004 | Kamoshita .............. F25B 9/145 62/615 |
| 2006/0133955 | A1 | * | 6/2006 | Peters ................. C23C 16/4481 422/63 |

* cited by examiner

SYSTEM AND METHOD FOR REFILLING CRYOGEN IN MICROSCOPE CRYOGEN HOLDERS

RELATED APPLICATIONS AND CLAIM OF PRIORITY

This patent document claims priority to U.S. Provisional Patent Application No. 62/379,838, filed Aug. 26, 2016, the disclosure of which is fully incorporated into this document by reference.

BACKGROUND

As the resolving power of electron microscopes (or other types of microscopes) has improved, efforts to resolve high resolution structures of biological samples have been attempted. However, limitations to high resolution microscopic imaging are often set by the damage a specimen suffers during various sample preparation stages. Many laboratories use ultra-rapid freezing techniques to prepare biological specimens for examination in a microscope to avoid conformational changes of the specimen due to crystallization effects during sample preparation. This requires rapidly freezing a specimen for promoting the formation of amorphous ice, and maintaining the sample at temperatures well below −160° C. to prevent devitrification. Above approximately −160° C., the ice will adopt a crystalline form, which is detrimental to imaging and analysis.

Such frozen specimens require specific microscopes for imaging and analysis. For example, Cryo electron microscopy, or Cryo EM, is a powerful technique for studying frozen hydrated biological specimens in transmission electron microscopes. With respect to biological specimens, as indicated above, the specimen must also be maintained at a low temperature, preferably below −160° C. during the transfer, imaging and analysis process. A Cryo EM includes a specimen holder for mounting the specimen and maintaining it at the required low temperature through the use of a cryogen (or cooling medium) which reduces the temperature of portions of the specimen holder and the specimen itself. This cryogen (such as liquid nitrogen or liquid helium) is stored in an insulated container mounted to one end of the specimen holder, typically identified as a dewar. The dewar is a component of the specimen holder and it comprises an inner vessel enclosed within an evacuated housing. Typically, a dewar has a capacity to hold 0.2-0.5 liters of cryogen and imaging needs to be stopped every 2-3 hours for manual refilling of the dewar. This has many drawbacks, such as limiting the automatic data acquisition time to 2-3 hours, imaging errors because of recalibration required after refilling, manual intervention that leads to inefficiency because a microscope cannot be used when a technician is unavailable, possibility of specimen spoiling during refilling, specimen dislocation, or the like. It is not possible to increase the capacity of a dewar because of the weight restrictions placed on parts of a microscope. Other parts of a microscope such as an anti-contamination device, specimen holder itself, etc. may also require refilling during the operation of the microscope.

This document describes a cryogen refilling system that is directed to solving the issues described above, and/or other problems.

SUMMARY

In some embodiments, a cryogen refilling for a microscope cryogen holder may include a reservoir assembly for holding cryogen, a delivery channel in fluid communication with the reservoir assembly for delivering cryogen from the reservoir assembly to a microscope cryogen holder, a sensor-lid assembly comprising a sensor assembly configured to detect sensor data corresponding to a level of cryogen in the microscope cryogen holder, and a controller. The delivery channel may also include at least one control valve. The controller may further include a processor in communication with the sensor assembly, and a computer-readable medium containing programming instructions. The processor may be configured to receive sensor data from the sensor assembly, analyze the sensor data to determine whether the microscope cryogen holder requires refilling, and in response to determining that the microscope cryogen holder requires refilling, cause a valve control mechanism to open the at least one control valve of the delivery channel.

In one or more embodiments, the sensor assembly may include a probe element comprising a first end and a second end. The first end of the probe element is in contact with liquid cryogen in the microscope cryogen holder when the microscope cryogen holder does not require refilling, and a temperature of the second end the probe element changes when the first end is in contact with liquid cryogen in the microscope cryogen holder compared to when the first end is not in contact with liquid cryogen. In certain embodiments, the probe element may also include a sensor element configured to collect temperature data corresponding to a temperature of the second end and transmit the temperature data to the processor. In certain such embodiments, the processor may analyze the temperature data to determine whether the microscope cryogen holder requires refilling by determining whether the temperature of the second end is above a threshold temperature. The threshold temperature may be about 20° C. to about −100° C., about 10° C. to about −90° C., about 0° C. to about −80° C., about −10° C. to about −70° C., about −20° C. to about −60° C., about −30° C. to about −50° C., about 20° C., about 10° C., about 0° C. about −10° C., about −20° C., about −30° C., about −40° C., about −50° C., about −60° C., about −70° C., about −80° C., about −90° C., about −100° C.

In some embodiments, the sensor-lid assembly may also include a lid assembly configured to be mounted over an opening of the microscope cryogen holder. In such embodiments, the lid assembly may include a first opening configured to receive the sensor assembly, and a second opening configured to receive a delivery nozzle, wherein the delivery nozzle is in fluid communication with the delivery channel. In at least one such embodiment, the second opening may be configured to receive the delivery channel via a nozzle receiving component that has a reentrant tube design.

In certain embodiments, the sensor assembly is configured to have a reentrant tube design.

In some embodiments, the cryogen refilling system may further include a support frame. The support frame may include an arm segment and a vertical segment, and the reservoir assembly may be mounted on the arm segment via a sliding unit. The sliding unit may be configured to move the reservoir assembly along an axis parallel to a length of the arm segment.

In one or more embodiment, the processor may further be configured to, in response to determining that the microscope cryogen holder requires refilling, cause movement of at least one component of the cryogen refilling system such that the reservoir assembly is positioned to supply liquid cryogen to the microscope cryogen holder, before causing the valve control mechanism to open the at least one control valve of the delivery channel.

In certain embodiment, the reservoir assembly may configured to supply cryogen to the microscope cryogen holder using gravity feeding, an external pump, and/or pressure feeding.

In an embodiment, the reservoir assembly may be configured to hold about 5 litres to about 25 litres of liquid cryogen.

In an embodiment, the sensor assembly may include a sensor element configured to collect sensor data corresponding to a change in cryogen level of the microscope cryogen holder and transmit the sensor data to the processor. In such an embodiment, the sensor element may be an ultrasound sensor.

In some embodiments, the processor may further be configured to, after causing the valve control mechanism to open the at least one control valve of the delivery channel: analyze the sensor data to determine whether the cryogen level in the microscope cryogen holder has reached a threshold level, and in response to determining that the cryogen level in the microscope cryogen holder has reached the threshold level, cause the valve control mechanism to close the at least one control valve of the delivery channel.

In another aspect of this disclosure, a method for automatically refilling cryogen in a microscope cryogen holder may include, by a processor, receiving temperature data from a sensor assembly of a cryogen refilling system, analyzing the temperature data to determine whether a microscope cryogen holder requires refilling, and in response to determining that the microscope cryogen holder requires refilling, by the processor, cause a valve control mechanism to open a control valve of a delivery channel in fluid communication with a cryogen reservoir assembly.

In some embodiments, analyzing the temperature data to determine whether the microscope cryogen holder requires refilling may include determining whether temperature of one end of a probe element of the sensor assembly is above a threshold temperature.

In certain embodiments, the method may also include, by the processor, after causing the valve control mechanism to open the control valve of the delivery channel: analyzing the temperature data to determine whether the cryogen level in the microscope cryogen holder has reached a threshold level, and in response to determining that the cryogen level in the microscope cryogen holder has reached the threshold level, causing the valve control mechanism to close the control valve of the delivery channel.

In yet another aspect, cryogen refilling system for a microscope cryogen holder, may include a reservoir assembly for holding cryogen, a delivery channel in fluid communication with the reservoir assembly for delivering cryogen from the reservoir assembly to a microscope cryogen holder, a sensor-lid assembly comprising a sensor assembly configured to detect sensor data corresponding to a level of cryogen in the microscope cryogen holder, and a controller. The delivery channel may include at least one control valve. The controller may include a processor in communication with the sensor assembly, and a computer-readable medium containing programming instructions. The processor may be configured to: periodically, cause a valve control mechanism to open the at least one control valve of the delivery channel to deliver cryogen to the microscope cryogen holder, receive sensor data from the sensor assembly, analyze the sensor data to determine whether cryogen level in the microscope cryogen holder has reached a threshold level, and in response to determining that the cryogen level in the microscope cryogen holder has reached the threshold level, cause the valve control mechanism to close the at least one control valve of the delivery channel.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

When used in this document, terms such as "top" and "bottom," "upper" and "lower", or "front" and "rear," are not intended to have absolute orientations but are instead intended to describe relative positions of various components with respect to each other. For example, a first component may be an "upper" component and a second component may be a "lower" component when a light fixture is oriented in a first direction. The relative orientations of the components may be reversed, or the components may be on the same plane, if the orientation of a light fixture that contains the components is changed. The claims are intended to include all orientations of a device containing such components.

The term "cryogen" includes both liquid and gaseous cryogens as both may be used in various implementations of the different embodiments described in this document. Examples may include liquid nitrogen, an inert fluid (such as neon or helium), liquid carbon dioxide, or the like.

The term "microscope cryogen holder" refers to a component of a microscope that is used to store cryogen for use in various microscopic processes and/or functions. Examples may include, without limitation, a dewar, an anti-contamination device, specimen holder, or the like.

The terms "computer-readable medium," "data storage facility," and "memory" each refer to a non-transitory device on which computer-readable data, programming instructions or both are stored. Unless the context specifically states that a single device is required or that multiple devices are required, the terms "computer-readable medium," "data storage facility," and "memory" include both the singular and plural embodiments, as well as portions of such devices such as memory sectors.

In this document, the terms "processor" and "processing device" refer to a hardware component of an electronic device that is configured to execute programming instructions. The term "processor" may refer to either a single processor or to multiple processors that together implement various steps of a process. Unless the context specifically states that a single processor is required or that multiple processors are required, the term "processor" includes both the singular and plural embodiments.

Figure 1:
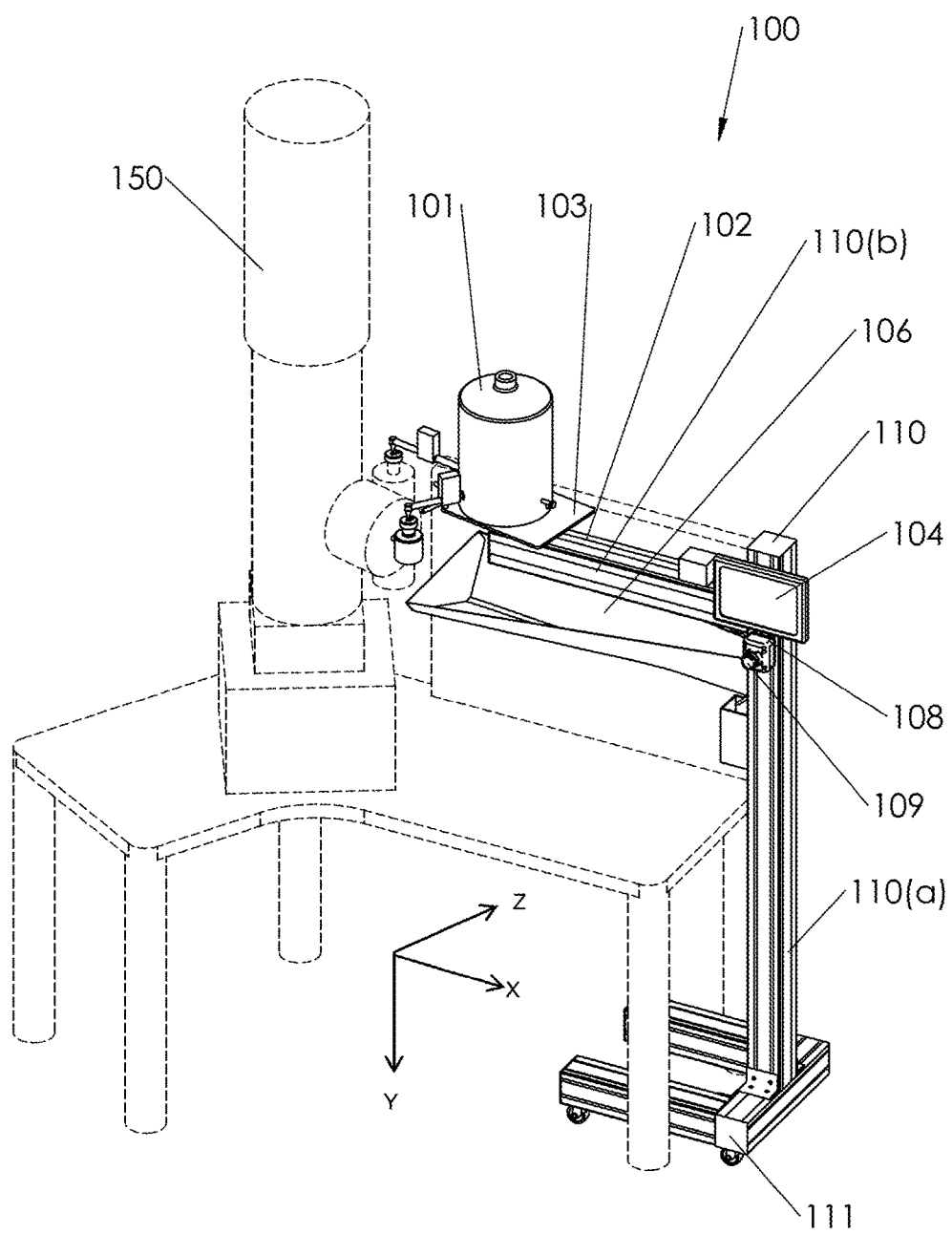
FIG. 1 illustrates a front perspective view of an example cryogen refilling system, according to an embodiment.

FIG. 1 illustrates a side perspective view of one embodiment of a cryogen refilling system 100 disclosed in this document in communication with a microscope assembly 150. FIG. 1 illustrates one embodiment of a cryogen refilling station that includes a reservoir assembly 101 mounted on a support frame 110, via a sliding unit 102 and an optional base 103. The cryogen refilling station also includes a collection tray 106 and a user interface 104. The frame 110 includes two segments 110(a) and 110(b) and may be attached to a base assembly 111. The cryogen refilling station may also include, without limitation, one or more sensors, shut-off valves or switches, processing devices, or the like.

The cryogen refilling station may include more or less components than those shown in FIG. 1. However, the components shown are sufficient to disclose an illustrative embodiment implementing the present solution. The components of the cryogen refilling station 100 can be adapted to, arranged to and/or programmed to perform one or more of the methodologies, procedures, or functions described herein.

As shown in FIG. 1, an example cryogen refilling system 100 may include a reservoir assembly 101 mounted on a support frame 110 via a sliding unit 102. The reservoir assembly 101 may be configured to store and deliver of cryogen to a microscope cryogen holder.

In certain embodiments, the support frame 110 may be a support assembly configured to mount a reservoir assembly and accurately position the reservoir assembly with respect to a microscope assembly for cryogen refilling. In some embodiments, the support frame 110 may include a vertical segment 110(a) connected to an arm segment 110(b) such that the arm segment 110(b) may rotate about an axis parallel (Y-axis) to the length of the vertical segment 110(a). Alternatively and/or additionally, the arm segment 110(b) may also move (rectilinearly) in a direction along an axis parallel to the length of the vertical segment 110(a) (i.e., move in +/−Y direction). Such movement of the arm segment 110(b) may be achieved by, for example, an electric motor, hydraulic cylinder, magnetic cylinder, pneumatic cylinder, or the like. As used herein, the phrase "vertical segment" generally refers to a vertically disposed, and the phrase "arm segment" generally refers to a horizontally disposed structure mounted on the vertical segment. However, these definitions should not be construed as limiting to the possibility of other embodiments in which vertical segments are other than generally vertical and/or in which arm segments are other than generally horizontal. It should also be noted that the support member 110 may include more than one arm segments, each configured to include a reservoir assembly.

In some embodiments, the vertical segment 110(a) of the support frame 110 may be attached to a base assembly 111 configured to provide a stable support to the bottom of the vertical segment 110(a). In some embodiments, the base assembly 111 may include wheels or other mechanisms to aid in easy movement of a cryogen refilling system 100. Alternatively and/or additionally, the base assembly 111 may allow for movement of the cryogen refilling system, and may be stationary. It should be understood to those skilled in the art that while the current disclosure describes a floor standing cryogen refilling system, other configurations such as without limitation, microscope mounted, wall mounted, or dropped from a ceiling, are within the scope of this disclosure. It should also be understood that other support frame structures and configurations are within the scope of this disclosure.

As shown in FIG. 1, a reservoir assembly 101 may be mounted on the arm segment 110(b) of the support frame 110 via a sliding unit 102 configured to move the reservoir assembly 101 along an axis parallel to the length of the arm segment 110(b) (+/−X direction). The sliding unit 102 may use any now or hereafter known methods for moving the reservoir assembly 101 such as, without limitation, rails, strings, grooves, gears, or the like. In certain embodiments, the reservoir assembly 101 may directly engage and/or associate with the sliding unit 102. Alternatively and/or additionally, the reservoir assembly 101 may be configured to be placed on a platform (such as a mounting stage) 103, which in turn associates with and/or engages the sliding unit 102.

In some embodiments, the vertical segment 110(a), the arm segment 110(b), the base assembly 111, the sliding unit 102, and/or other components of the cryogen refilling system 100 may include one or more position sensors such as, without limitation, limit position sensors, magnetic sensors, or the like, for detecting the position of the reservoir assembly 101 and/or various other components of the cryogen refilling system.

In some embodiments, the movement of various components of the cryogen refilling system 100 such as, the vertical segment 110(a), the arm segment 110(b), the base assembly 111, the sliding unit 102, may be controlled manually and/or automatically. For example, in certain embodiments, rotational movement of the arm segment 110(b) about an axis parallel (Y-axis) to the length of the vertical segment 110(a), movement of the arm segment 110(b) in a direction along an axis parallel to the length of the vertical segment 110(a) (+/−Y direction), movement of the base assembly 111, and/or movement of the sliding unit 102 may be controlled by one or more actuator devices (such as a motor) that may receive control signals from a controller (discussed below in detail), and may cause movement of a corresponding component of the cryogen refilling system 100 based on the control signals and/or the information received from one or more position sensors. Alternatively and/or additionally, a user may manually cause the movement of one or more components of the cryogen refilling system 100.

In an example embodiment, a reservoir assembly 101 of a cryogen refilling system 100 may be positioned proximately to one or more components of a microscope assembly 150 that require cryogen refills. In some embodiments, movement of one or more components of the cryogen refilling system 100 may be controlled to control the positioning of the reservoir assembly 101 by sending control signals to one or more actuators that control the movement of various cryogen refilling system components. Examples may include, controlling movement of the base assembly 111, controlling movement of the arm segment 110(b) along an axis parallel to the length of the vertical segment 110(a), controlling rotation of the arm segment 110(b) about an axis parallel to the length of the vertical segment 110(a), controlling movement of the reservoir assembly 101 along an axis parallel to the length of the arm segment 110(b) via a sliding unit 102, or a combination thereof.

Referring back to FIG. 1, the cryogen refilling system 100 may also include a collection tray 106 configured to be placed under the arm segment 110(b) for receiving liquid drips such as the cryogen and condensed water vapor to prevent liquid drip onto microscope components and for user safety. In some embodiments, upon completion of a refilling task, the sliding unit 102 may operate to move the reservoir assembly 101 away from a microscope cryogen holder and over the collection tray 106 such that the liquid drip is collected only in the collection tray 106, in order to prevent liquid drip onto various microscope components and for user safety.

In certain embodiments, the cryogen refilling system 100 may further include a user interface 104 configured to transmit and/or receive one or more instructions to and/or from a user. Example may include, without limitation, a keypad, a touchscreen, an audio interface, a display, or the like. Examples of instructions may include, without limitation, positional and/or directional information. Examples of user instructions may include without limitation, a refill duration and intervals between multiple refills.

In some embodiments, the cryogen refilling system 100 may also include a controller (not show here) configured to (i) receive data from a sensor unit of a reservoir assembly, (ii) analyze the data to determine if a microscope cryogen holder (such as a dewar) requires refilling, and (iii) automatically control the positioning of the reservoir assembly and opening/closing of various valves in response to the above determination, as discussed below with respect to FIG. 5. The term "controller" as used herein is intended in its broadest sense as a device that includes at least one processor, and optionally further circuitry, memory, and/or logic, for controlling and/or providing at least some aspects of the cryogen refilling station operations (illustrated in FIG. 6 below). In some embodiments, the processor of the controller in electronic communication with the other components of the cryogen refilling system 100. The processor may also be in communication with a clock module and receive time data generated by the clock module for use in various methods described below. In certain embodiments, the processor may also control the positioning of the reservoir assembly 101 in response to user instructions (as discussed above). Some or all the components of the controller can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

Referring back to FIG. 1, the cryogen refilling system 100 may also include one or more sensors 108. Examples of such sensors may include, without limitation, oxygen sensors, temperature sensors, pressure sensors, contamination sensors, or the like. The cryogen refilling system 100 may further include various safety mechanisms such as an emergency shut-off switch 109. In some embodiments, the emergency shut-off switch 109 may be configured to manually shut down the cryogen refilling system 100 and/or close all control valves. For example, the emergency shut-off switch 109 may be configured to manually shut down the cryogen refilling system 100 upon detection of overfill, spillage, or the like.

Figure 2A:
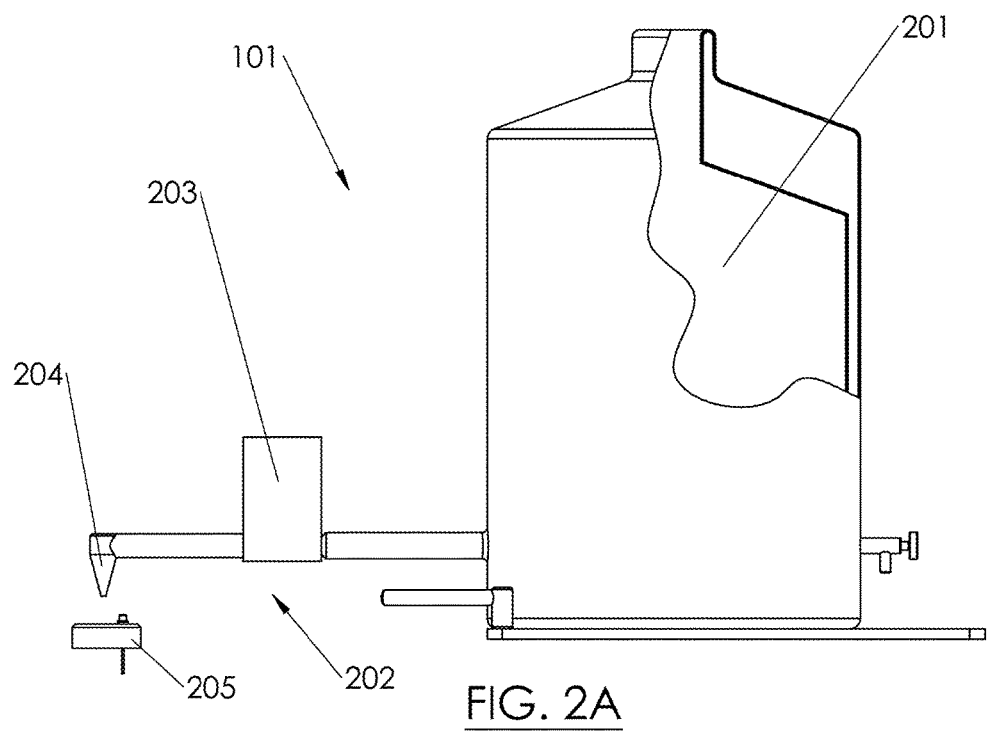
FIGS. 2A and 2B illustrate a side view and a top view respectively, of an example reservoir assembly of a cryogen refilling system, according to an embodiment.

As discussed above, the cryogen refilling system 100 includes a reservoir assembly 101 for storage and delivery of cryogen to a microscope cryogen holder. FIG. 2A illustrates an expanded view of a reservoir assembly 101 of a cryogen refilling system 100. As shown in FIG. 2A, the reservoir assembly 101 includes a storage chamber 201 in fluid communication with a cryogen delivery nozzle 204 via a delivery channel 202. The delivery channel includes at least one flow control valve 203. It will be understood to those skilled in the art that while the reservoir assembly 101 of FIG. 2A illustrates one cryogen delivery nozzle 204 and one delivery channel 202, the reservoir assembly 101 may include a plurality of delivery nozzles, delivery channels, and/or flow control valves.

Referring now to FIG. 2A, in certain embodiments, the storage chamber 201 may be configured to store and dispense cryogen to microscope components such as, without limitation, a dewar. The storage chamber 201 may include an inner volume enclosed within an evacuated housing to thermally insulate the cryogen stored in the storage chamber 201, and maintain the desired pressure and temperature. As such, the storage chamber 201 may hold the cryogen in liquid and/or gaseous state depending upon the temperature and/or pressures of the storage chamber 201.

In some embodiments, a position of the storage chamber 201 may be controlled (using the support frame 110) such that it is at an elevated height relative to a component of a microscope to be refilled. When so elevated, gravity alone may cause the cryogen to flow to the microscope cryogen holder from the storage chamber 201 from, for example, one or more channels near the bottom of the storage chamber 201 as shown in FIG. 2A, in a gravity feeding mechanism. Additionally and/or alternatively, an external pump (not shown here) may be used to supply the cryogen to a microscope cryogen holder. In yet another embodiment, cryogen may be delivered to a microscope cryogen holder using a pressure feeding mechanism from one or more delivery channels near the top of the storage chamber 201 (not shown here).

In some embodiments, the delivery channel 202 may be an insulated (e.g., vacuum jacketed) transfer conduit configured for transporting the cryogen. The insulation prevents freezing of the channels and minimizes losses during transport of the cryogen. A delivery channel may provide a fluid communication link between the storage chamber 201 and a cryogen delivery nozzle 204, and may include at least one flow control valve 203 for controlling the flow of cryogen through the delivery channel. In some embodiments, a flow control valve 203 may be configured to turn on, off, reduce, increase, and/or otherwise control the flow of a cryogen in a one or more delivery channels in response to one or more instructions from a controller and/or a user. Examples of the flow control valve may include without limitation, pneumatic valves, solenoid valves, a check valve, or the like. In some embodiments, a flow control valve may include electromechanical control mechanisms such as, without limitation, electronic motors, solenoid valves, actuator valves, or the like, configured to control the opening and closing of the valve in response to control signals received from a controller.

In some embodiments, storage chamber 201 may be configured to hold about 5 liters to about 25 liters of cryogen. For example, the storage chamber may have a capacity of 5 liters, 10 liters, 15, liters, 20 liters, 5-10 liters, 10-15 liters, 15-20 liters, 20-25 liters, 5-15 liters, 10-20 liters, 15-25 liters, or the like.

Referring back to FIG. 2A, a cryogen delivery nozzle 204 may be configured to deliver cryogen from the storage chamber 201 to a microscope cryogen holder via a delivery channel 202. In certain embodiments, the cryogen delivery nozzle 204 may be configured to be received in a complementary nozzle receiving component of a sensor-lid assembly 205 (discussed below in detail with respect to FIG. 3) for delivery of cryogen from the delivery channel 202 to a microscope cryogen holder.

Figure 2B:
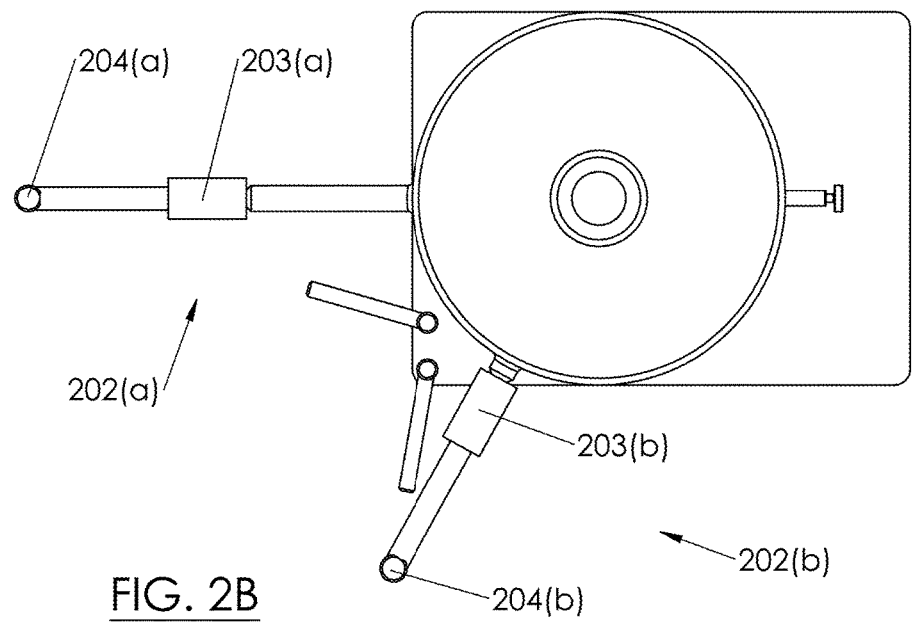

It should be understood to those skilled in the art that while the above disclosure describes filing of one microscope cryogen holder, cryogen levels in more than one microscope cryogen holder may be monitored and more than one microscope cryogen holder may be refilled using a cryogen refilling system simultaneously using the principles discussed in this disclosure. FIG. 2B illustrates a top view of a reservoir assembly 101 of a cryogen refilling system 100 that includes two delivery channels 202a and 202b that may simultaneously monitor and refill to microscope cryogen holders. Each delivery channel 202a and 202b includes a flow control valve 203a and 203b, and a cryogen delivery nozzle 204a and 204b, and a sensor-lid assembly (not shown here).

Figure 3:
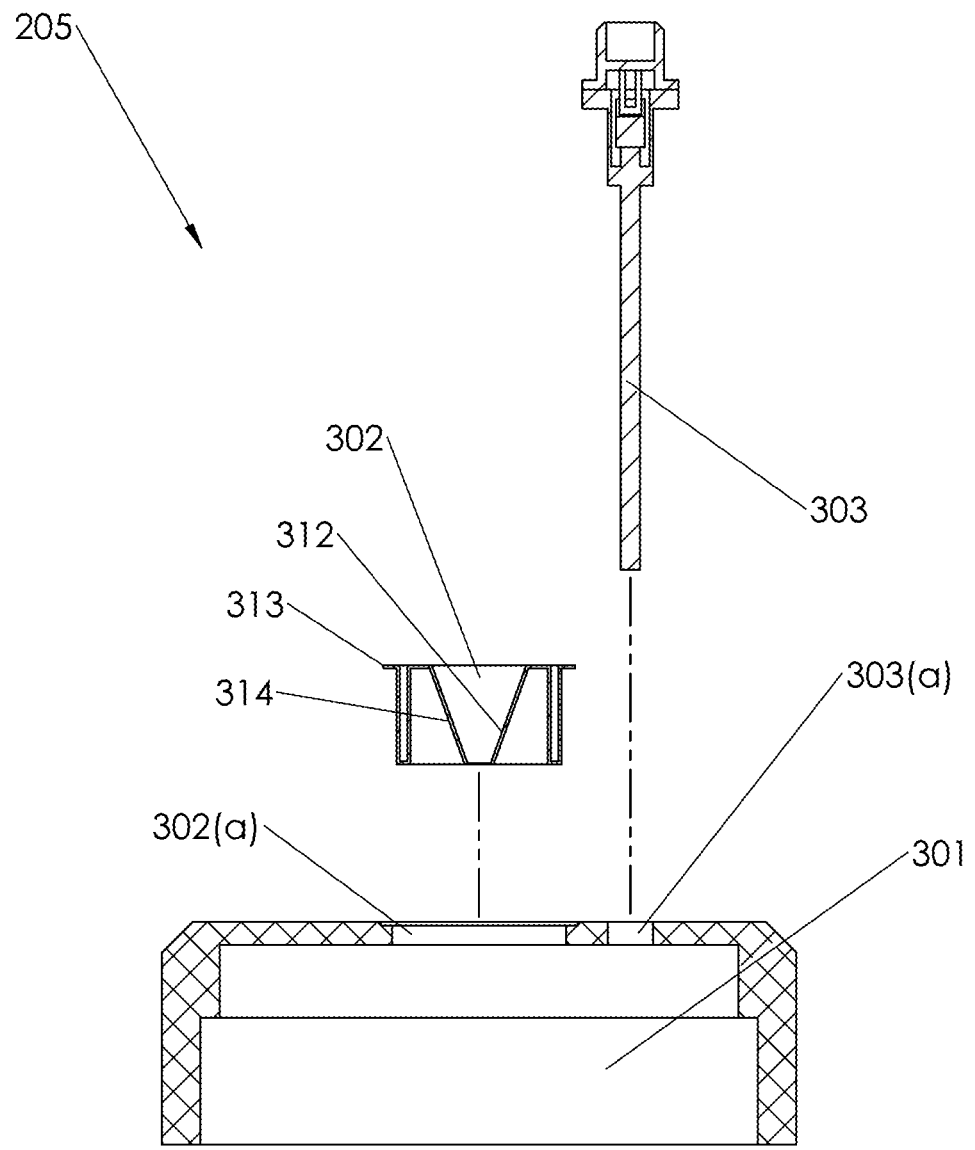
FIG. 3 illustrates a schematic expanded view of an example sensor-lid assembly of a cryogen refilling system, according to an embodiment.

Referring now to FIG. 3, it illustrates an expanded view of a sensor-lid assembly 205 configured to receive a delivery nozzle 204, according to an embodiment. The sensor-lid assembly 205 is configured to be mounted on top of a microscope cryogen holder that needs to be periodically refilled. In some embodiments, the sensor-lid assembly 205 may be custom designed to adapt to the opening of a microscope cryogen holder.

As shown in FIG. 3, the sensor-lid assembly 205 includes a lid assembly 301 configured to be mounted on top of a microscope cryogen holder that needs to be periodically refilled, and for receiving a nozzle receiving component 302. The sensor-lid assembly 205 also includes a sensory assembly 303 is configured to detect the level of liquid cryogen in a microscope cryogen holder that holds cryogen and needs to be periodically refilled.

In certain embodiments, the lid assembly 301 is configured to be mounted over an/or otherwise securely attach to an opening of a microscope cryogen holder that needs to be periodically refilled. For example, the lid assembly 301 may be mounted over an opening of a microscope cryogen holder using threads, a sealed interface, snap-fit interface, or the like. The lid assembly 301 may include a first opening 302(a) configured to receive a nozzle receiving component 302, and a second opening 303(a) configured to receive the sensor assembly 303. In some embodiments, the nozzle receiving component 302 may have a complementary shape to that of the cryogen delivery nozzle 204 (for example, a funnel shape) and may provide an interface for delivering the cryogen from the cryogen delivery nozzle 204 to a microscope cryogen holder via the lid assembly 301. In an alternate embodiment, the cryogen delivery nozzle 204 may directly be received into the opening 302(a), i.e. without a nozzle receiving component 302, and the opening 302(a) may be configured to have a complementary shape to that of the cryogen delivery nozzle 204.

In some embodiments, one or more components of the sensor-lid assembly 205 may include a reentrant tube design in order to minimize thermal losses and/or for keeping the lid assembly close to ambient temperatures. For example, in certain embodiments, the nozzle receiving component 302, the lid assembly 301, and/or the sensor assembly 303 may be configured to have a reentrant tube design. In FIG. 3, the nozzle receiving component 302 is shown to have a reentrant tube design. In a reentrant tube design configuration, an inner wall 312 of the nozzle receiving component 302 which may come in contact with the cryogen during refill is separated from an outer wall 313 of the nozzle receiving component 302 that engages and/or associates with the opening 302(a) of the lid assembly 301, via a series of interconnecting tubes 314. Such a reentrant tube design configuration increases the path length for thermal conduction from an inner cold surface in contact with the cryogen to an outer surface bonded at the lid-assembly 301 in order to provide thermal insulation. It will be understood to those skilled in the art that the number of interconnecting tubes may be determined based on the required thermal insulation. While FIG. 3 illustrates that a reentrant tube design configuration of a nozzle receiving component 302, similar design configurations can also be used for the lid assembly 301, and/or the sensor assembly 303.

In some embodiments, the one or more components of the sensor-lid assembly 205 may be manufactured using an insulator to prevent cryogen loss due to thermal leakage, and for maintaining the appropriate temperature and pressure inside the microscope cryogen holder.

In some embodiments, the sensory assembly 303 may be configured to detect the level of liquid cryogen in a microscope cryogen holder that holds cryogen and needs to be periodically refilled. The sensory assembly 303 may detect the level of liquid cryogen by, for example, monitoring temperature changes of a probe placed within the microscope cryogen holder (discussed below with respect to FIG. 4), by monitoring cryogen levels directly using an ultrasound sensor, or other suitable techniques. In certain embodiments, the sensor assembly may also have a reentrant tube configuration (not shown here), as described above, to increase the conduction path length from the cold sensor assembly to the bonded lid assembly.

Figure 4:
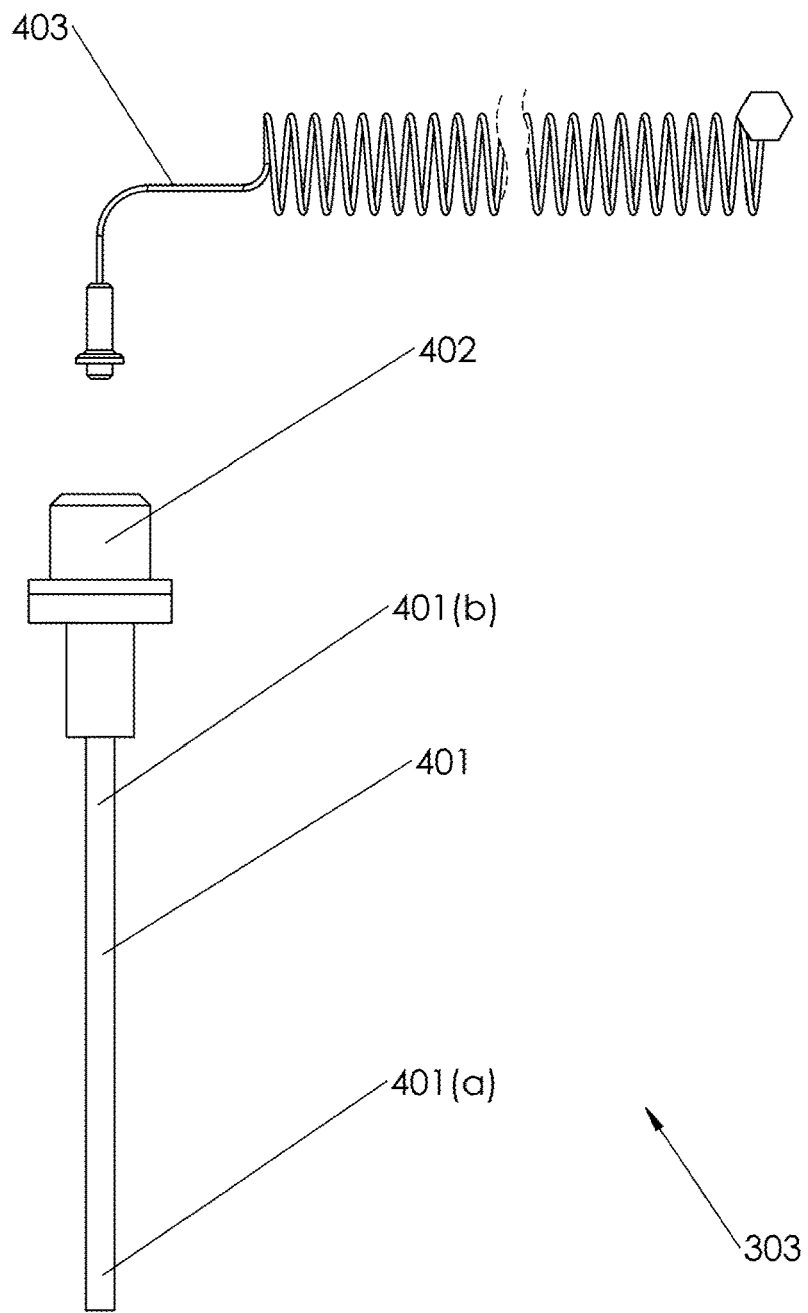
FIG. 4 illustrates a schematic view of an example sensor assembly of a cryogen refilling system, according to an embodiment.

Referring now to FIG. 4, it illustrates an example sensor assembly 303 configured to detect the level of liquid cryogen by monitoring temperature changes of a probe placed within a microscope cryogen holder. As shown in FIG. 4, the sensor assembly 303 may include a probe element 401 and a sensor element 402. The probe element 401 may include a rod, wire, or similar element configured to be placed in a microscope cryogen holder that holds cryogen and needs to be periodically refilled. A length of the probe element may be configured such that a lower end 401(a) of the probe element is in contact with the cryogen fluid in the microscope cryogen holder when the cryogen level in the microscope cryogen holder is adequate and no refilling is required. However, when the cryogen level in the microscope cryogen holder goes down below a threshold level and refilling is required, the probe element 401 does not contact the cryogen. The probe element is manufactured using a suitable material such that the temperature of the lower end 401(a) changes based on whether or not the lower end 401(a) is in contact with a cryogen, and is further configured to rapidly conduct the change in temperature along the length of the probe element to the upper end 401(b). For example, a suitable material is selected such that the temperature of the upper end 401(b) of the probe element changes in real time from about $(-100)°$ C.-$(-200)°$ C. when the lower end 401(a) of the probe element is in contact with liquid cryogen to about $20°$ C.-$(-100)°$ C. when the lower end 401(a) is not in contact with liquid cryogen (or vice versa). Example materials for manufacturing the probe element may include, without limitation, copper, stainless steel, ceramics, or the like.

The sensor element 402 of the sensor assembly 303 may include a temperature sensor in communication with an upper end 401(b) of the probe element 401 and configured to receive and/or analyze temperature data corresponding to the upper end 401(b). Hence, a sensor element may be configured to detect a temperature differential at the upper end of the probe element when the lower end of the probe element is in contact with liquid cryogen compared to when it is not in contact with liquid cryogen (and/or is in contact with a gaseous cryogen), and then may determine the level of liquid cryogen in a microscope cryogen holder.

In some embodiments, the temperature sensor 402 may be in direct contact with the upper end 401(b) of the probe element 401, by for example attaching the temperature sensor 402 to the upper end 401(b). Examples of such direct contact temperature sensors may include, without limitation, a thermocouple, a diode, a thermistor, a resistant thermometer, or the like. In an alternate embodiment, a temperature sensor may not be in direct contact with the upper end 401(b) of the probe element 401 (not shown here). Examples of such non-contact temperature sensors may include, without limitation, an optical sensor, an infrared (IR) sensor, a color temperature sensor, or the like, for non-contact temperature measurement configured to read the temperature of the upper end 401(b) from a suitable distance. In an example embodiment, a non-contact temperature sensor may be attached to the cryogen refilling system 100 at a suitable position to enable it to read the temperature of the upper end 401(b) from a suitable distance.

The temperature sensor may transmit the temperature data corresponding to the temperature of the upper end 401(b) to a controller of the cryogen refilling system 100 wirelessly and/or through a wired communication link 403, and the controller may analyze the received temperature data to determine the level of liquid cryogen in a microscope cryogen holder based on a temperature differential in the upper end 401(b). In some embodiments, the sensor assembly 303 may include a transmitter and/or receiver component (not shown here) for wireless communication of the temperature data from the temperature sensor to a controller and/or other components of a cryogen filling system. Additionally and/or alternatively, the sensor assembly 303 may communicate with a controller via a wired connection 403.

It will be understood to those skilled in the art that while the above description illustrates the use of a temperature sensor and probe assembly configured to monitor changes in cryogen levels in a microscope cryogen holder by monitoring and analyzing the temperature changes in a probe element, other types of sensors and/or probes may be used without deviating from the principles of this disclosure. For example, in an embodiment, an ultrasound sensor and/or ultrasonic sensor may be used to directly monitor the cryogen levels in a microscope cryogen holder. Other examples of sensors assemblies may include pressure sensors, capacitor level sensors, radar sensors, visual sensors, or the like configured to measure the cryogen levels in a microscope cryogen holder.

Figure 5:
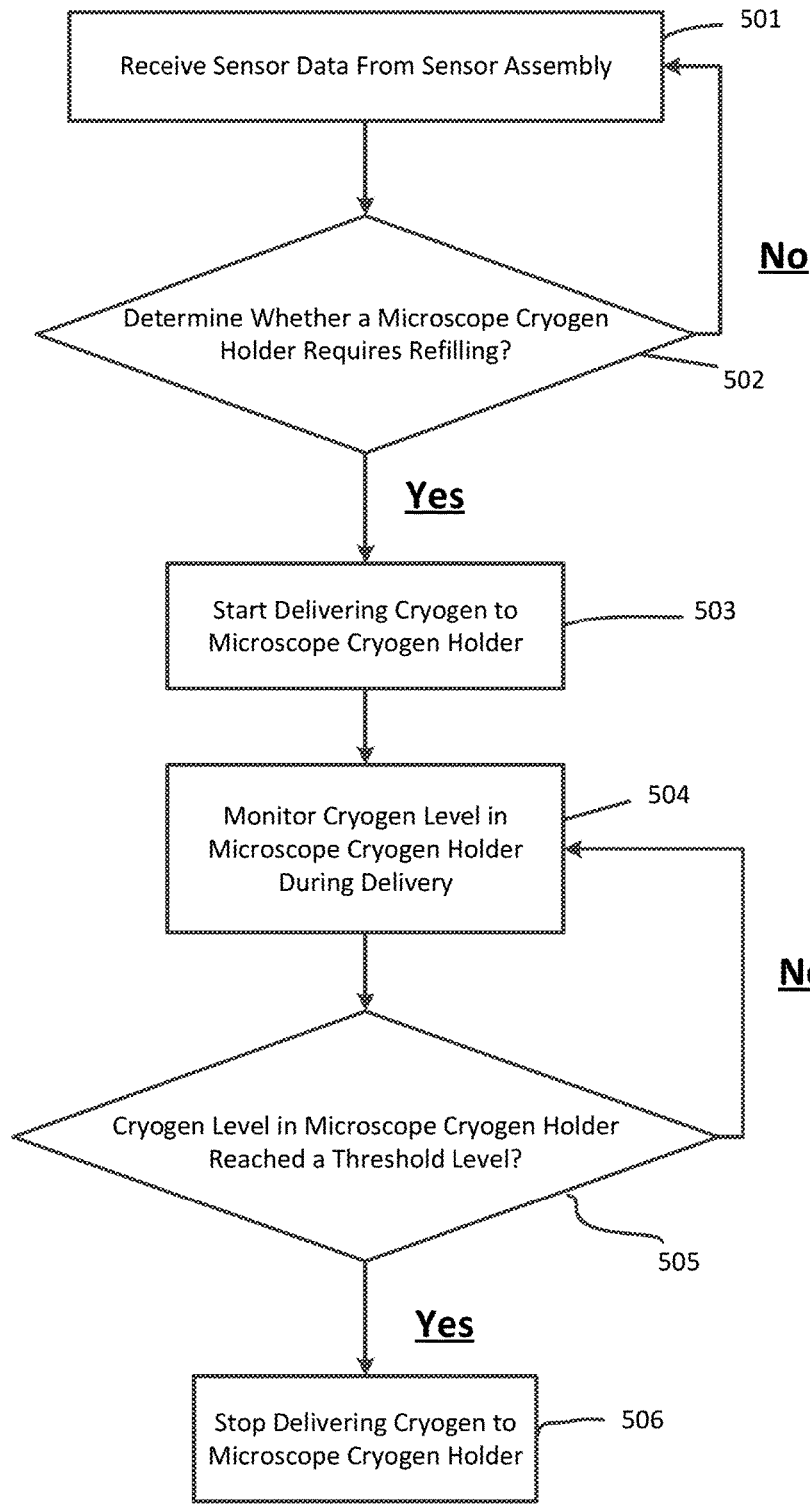
FIG. 5 is a flowchart illustrating an example method for automatically refilling a microscope cryogen holder using a cryogen refilling system, according to an embodiment.

FIG. 5 illustrates a flowchart in accordance with one embodiment illustrating and describing a method for monitoring cryogen level in a microscope cryogen holder, refilling the microscope cryogen holder when the cryogen level is below a threshold level, and/or preventing overflow of cryogen. While the method 500 is described for the sake of convenience and not with an intent of limiting the disclosure as comprising a series and/or a number of steps, it is to be understood that the process does not need to be performed as a series of steps and/or the steps do not need to be performed in the order shown and described with respect to FIG. 5, but the process may be integrated and/or one or more steps may be performed together, or the steps may be performed in the order disclosed or in an alternate order.

As shown in FIG. 5, the cryogen refilling system may receive sensor data 501 from the sensor assembly. In an embodiment, the received sensor data may be temperature data corresponding to a probe element placed in a microscope cryogen holder detected by a temperature sensor of the sensor assembly. Alternatively and/or additionally, the system may receive cryogen level data from the sensor assembly from sensors such as an ultrasound sensor, an ultrasonic sensor, a radar sensor, or the like. The cryogen refilling system may receive the sensor data continuously, at specific time intervals, upon detecting a trigger event, or a combination thereof. Examples of trigger events may include without limitation, detecting that cryogen in a microscope cryogen holder is being used (such as during imaging), specimen preparation or the like. For example, the cryogen refilling system may receive the sensor data continuously and/or at specific time intervals after detecting a trigger event. In some embodiments, the time interval may correspond to the time it may take for the cryogen in a microscope cryogen holder to get used up (such as 2-3 hrs. for a dewar).

In step 502, the cryogen refilling system may analyze the received sensor data to determine if the microscope cryogen holder requires refilling. For example, the cryogen refilling system may determine that the microscope cryogen holder requires refilling if temperature of a probe element (and/or an upper end of the probe element) of the sensor assembly is above a first threshold temperature. Temperature of an upper end of the probe element above the first threshold temperature is indicative that the lower end of the probe element is not in contact with liquid cryogen in a microscope cryogen holder. Example threshold temperatures may include, without limitations, about 20° C. to about −100° C., about 10° C. to about −90° C., about 0° C. to about −80° C., about −10° C. to about −70° C., about −20° C. to about −60° C., about −30° C. to about −50° C., about 20° C., about 10° C., about 0° C. about −10° C., about −20° C., about −30° C., about −40° C., about −50° C., about −60° C., about −70° C., about −80° C., about −90° C., about −100° C., or the like. Additionally and/or alternatively, the system may determine that the microscope cryogen holder requires refilling if the cryogen level detected using, for example, an ultrasound sensor, is below a first threshold level.

It will be understood to those skilled in the art that while FIG. 5 describes determining whether the microscope cryogen holder requires refilling by analyzing sensor data, the cryogen refilling system may determine that the microscope cryogen holder requires refilling using alternate methods without deviating from the principles of this disclosure. For example, the cryogen refilling system may determine that the microscope cryogen holder requires refilling at specific time intervals, upon detecting a trigger event, or a combination thereof. In some embodiments, the time interval may correspond to the time it may take for the cryogen in a microscope cryogen holder to get used up (such as 2-3 hrs. for a holder dewar) after detection of a trigger event. Examples of trigger events may include without limitation, detecting that cryogen in a microscope cryogen holder is being used (such as during imaging), specimen preparation, user instructions, or the like.

In response to determining that that a microscope cryogen holder requires refilling, the cryogen refilling system may start delivering 503 cryogen to the microscope cryogen holder that requires refilling. In certain embodiments, for delivering cryogen to the microscope cryogen holder the cryogen refilling system may position the reservoir assembly in a desired position proximate to the microscope cryogen holder by, for example, sending control signals to one or more actuators that control the movement of various cryogen refilling system components. The system may also cause a valve control mechanism (such as an actuator) to open one or more control valves for a delivery channel that is in fluid communication with the microscope cryogen holder (e.g., via the lid assembly and the delivery nozzle).

During refilling, the cryogen refilling system may continuously monitor 504 the cryogen level in the microscope cryogen holder to determine 505 whether the cryogen level in the microscope cryogen holder has reached a threshold level. The cryogen refilling system may stop delivering cryogen to the microscope cryogen holder if the cryogen level has reached a threshold level, in order to prevent overfilling and/or spillage. In an embodiment, the cryogen refilling system may monitor the cryogen level in the microscope cryogen holder by receiving and analyzing sensor data from the sensor assembly. For example, the cryogen refilling system may receive temperature data corresponding to an upper end of a probe element and may analyze the received temperature data to determine if the temperature of a lower end of the probe element (that contacts the liquid cryogen when cryogen level is adequate) of a sensor assembly is below a second threshold temperature. Temperature of the upper end of the probe element below the second threshold temperature is indicative that the lower end of probe element is in contact with liquid cryogen in a microscope cryogen holder, i.e., the cryogen level in the microscope cryogen holder is adequate (i.e., at a threshold level) and cryogen delivery should be stopped. Example threshold temperatures may include, without limitations, about −100° C. to about −200° C., about −110° C. to about −190° C., about −120° C. to about −180° C., about −130° C., about −160° C., about −140° C., about −150° C., about −196° C., about −100° C., about −110° C., about −120° C., about −130° C., about −140° C., about −150° C., about −160° C., about −170° C., about −180° C., about −190° C., about −200° C., or the like. Additionally and/or alternatively, the system may receive cryogen level data using, for example, an ultrasound sensor. In such an embodiment, the cryogen refilling system may determine that the delivery of cryogen should be stopped if cryogen level in the microscope cryogen holder is above a second threshold level.

In response to determining that the cryogen level in the microscope cryogen holder has reached a threshold level, the cryogen refilling system may stop 506 delivering the cryogen by closing one or more control valves for the delivery means.

In an alternate embodiment, the cryogen refilling system may stop refilling after a pre-determined time, where the pre-determined time may be indicative of the time it takes to fill cryogen in a microscope cryogen holder to a desired level.

Figure 6:
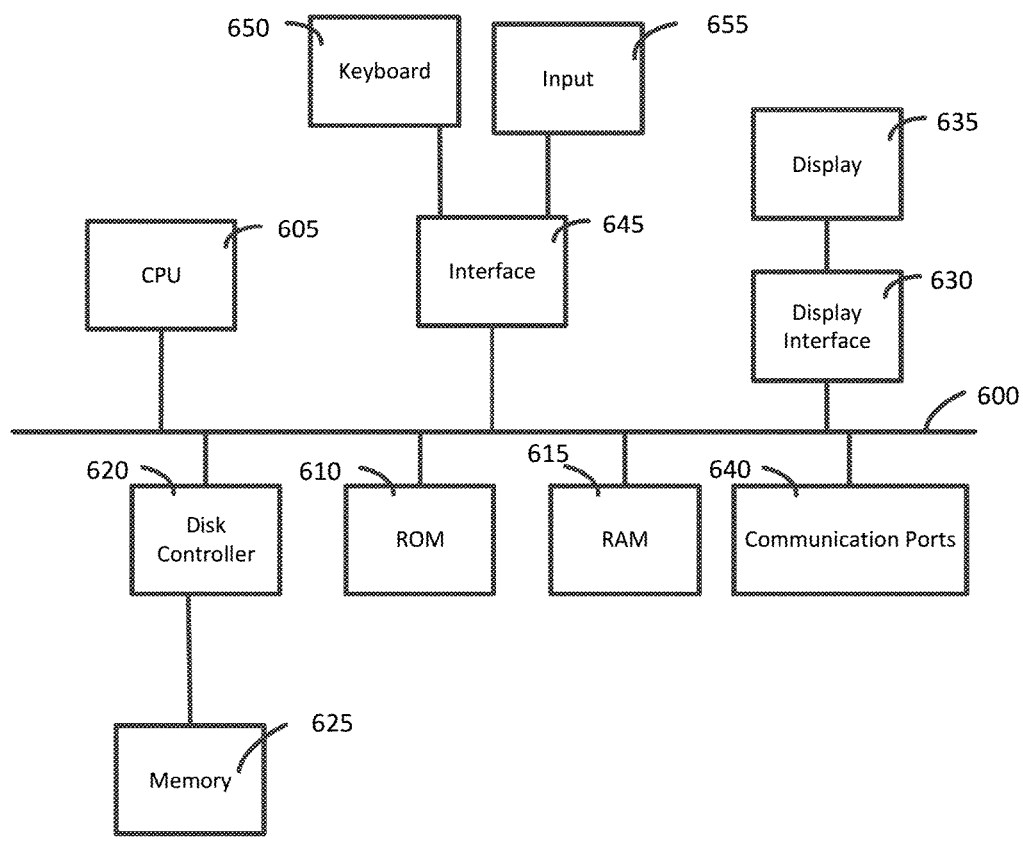
FIG. 6 illustrates a block diagram of example of internal hardware that may be used to contain or implement the various computer processes and systems, according to an embodiment.

FIG. 6 depicts an example of internal hardware that may be used to contain or implement the various computer processes and systems as discussed above. For example, the cryogen filling system discussed above may include hardware such as that illustrated in FIG. 6. An electrical bus 600 serves as an information highway interconnecting the other illustrated components of the hardware. A computing device will include one or more processors. CPU 605 is a central processing unit of the system, performing calculations and logic operations required to execute a program. CPU 605, alone or in conjunction with one or more of the other elements disclosed in FIG. 6, is a processing device, computing device or processor as such terms are used within this disclosure. As used in this document, the terms "processor" and "processing device" may include a single processor or a group of processors that collectively execute programming instructions to perform various steps of a process. Read only memory (ROM) 610 and random access memory (RAM) 615 constitute examples of memory devices. As used in this document, the terms "computer-readable medium," "memory" or "memory device" are used interchangeably and may include a single memory device, a group of memory devices, or a sector or other subdivision of such a device.

A controller 620 interfaces with one or more optional memory devices 625 that service as data storage facilities to the system bus 600. These memory devices 625 may include, for example, an external DVD drive or CD ROM drive, a hard drive, flash memory, a USB drive, a distributed storage medium such as a cloud-based architecture, or another type of device that serves as a data storage facility. As indicated previously, these various drives and controllers are optional devices. Additionally, the memory devices 625 may be configured to include individual files for storing any software modules or instructions, auxiliary data, incident data, common files for storing groups of contingency tables and/or regression models, or one or more databases for storing the information as discussed above.

Programming instructions, software or interactive modules for performing any of the functional steps associated with the processes as described above may be stored in the ROM 610 and/or the RAM 615. Optionally, the program instructions may be stored on a tangible computer readable medium such as a compact disk, a digital disk, flash memory, a memory card, a USB drive, an optical disc storage medium, a distributed storage medium such as a cloud-based architecture, and/or other recording medium.

A display interface 630 may permit information from the bus 600 to be displayed on the display 635 in audio, visual, graphic or alphanumeric format. Communication with external devices may occur using various communication ports 640. A communication port 640 may be attached to a communications network, such as the Internet, a local area network or a cellular telephone data network.

The hardware may also include an interface 645 which allows for receipt of data from input devices such as a keyboard 650 or other input device 655 such as a remote control, a pointing device, a video input device and/or an audio input device.

The features and functions described above, as well as alternatives, may be combined into many other systems or applications. Various presently unforeseen or unanticipated alternatives, modifications, variations or improvements may be made by those skilled in the art, each of which is also intended to be encompassed by the disclosed embodiments.

The invention claimed is:

1. A cryogen refilling system for a microscope cryogen holder, comprising:
   a reservoir assembly for holding cryogen;
   a delivery channel in fluid communication with the reservoir assembly for delivering cryogen from the reservoir assembly to a microscope cryogen holder, wherein the delivery channel comprises at least one control valve;
   a sensor-lid assembly comprising:
      a sensor assembly configured to detect sensor data corresponding to a level of cryogen in the microscope cryogen holder, and
      a lid assembly configured to be mounted over an opening of the microscope cryogen holder, the lid assembly further comprising:
         a first opening configured to receive the sensor assembly, and a second opening configured to:
receive a delivery nozzle via a nozzle receiving component that has a reentrant tube design, wherein the delivery nozzle is in fluid communication with the delivery channel; and
a controller, wherein the controller comprises:
a processor in communication with the sensor assembly, and
a computer-readable medium containing programming instructions that are configured to, when executed by the processor, cause the processor to:
receive sensor data from the sensor assembly,
analyze the sensor data to determine whether the microscope cryogen holder requires refilling, and
in response to determining that the microscope cryogen holder requires refilling, cause a valve control mechanism to open the at least one control valve of the delivery channel.

2. The cryogen refilling system of claim 1, wherein the sensor assembly comprises:
a probe element comprising a first end and a second end, wherein:
the first end of the probe element is in contact with liquid cryogen in the microscope cryogen holder when the microscope cryogen holder does not require refilling, and
a temperature of the second end the probe element changes when the first end is in contact with liquid cryogen in the microscope cryogen holder compared to when the first end is not in contact with liquid cryogen; and
a sensor element configured to collect temperature data corresponding to a temperature of the second end and transmit the temperature data to the processor.

3. The cryogen refilling system of claim 2, wherein the programming instructions that are configured to, when executed by the processor, cause the processor to analyze the temperature data to determine whether the microscope cryogen holder requires refilling, further comprise instructions to determine whether the temperature of the second end is above a threshold temperature.

4. The cryogen refilling system of claim 3, wherein the threshold temperature is selected from the group comprising: about 20° C. to about −100° C., about 10° C. to about −90° C., about 0° C. to about −80° C., about −10° C. to about −70° C., about −20° C. to about −60° C., about −30° C. to about −50° C., about 20° C., about 10° C., about 0° C. about −10° C., about −20° C., about −30° C., about −40° C., about −50° C., about −60° C., about −70° C., about −80° C., about −90° C., about −100° C.

5. The cryogen refilling system of claim 1, wherein the sensor assembly is configured to have a reentrant tube design.

6. The cryogen refilling system of claim 1, further comprising a support frame, wherein:
the support frame comprises an arm segment and a vertical segment; and
the reservoir assembly is mounted on the arm segment via a sliding unit.

7. The cryogen refilling system of claim 6, wherein the sliding unit is configured to move the reservoir assembly along an axis parallel to a length of the arm segment.

8. The cryogen refilling system of claim 1, further comprising programming instructions that are configured to, when executed by the processor, cause the processor to, in response to determining that the microscope cryogen holder requires refilling, cause movement of at least one component of the cryogen refilling system such that the reservoir assembly is positioned to supply liquid cryogen to the microscope cryogen holder, before causing the valve control mechanism to open the at least one control valve of the delivery channel.

9. The cryogen refilling system of claim 1, wherein the reservoir assembly is configured to supply cryogen to the microscope cryogen holder using one or more of the following: gravity feeding, an external pump, or pressure feeding.

10. The cryogen refilling system of claim 1, wherein the reservoir assembly is configured to hold about 5 litres to about 25 litres of liquid cryogen.

11. The cryogen refilling system of claim 1, wherein the sensor assembly comprises a sensor element configured to collect sensor data corresponding to a change in cryogen level of the microscope cryogen holder and transmit the sensor data to the processor.

12. The cryogen refilling system of claim 11, wherein the sensor element comprises an ultrasound sensor.

13. The cryogen refilling system of claim 1, further comprising programming instructions that are configured to, when executed by the processor, cause the processor to, after causing the valve control mechanism to open the at least one control valve of the delivery channel:
analyze the sensor data to determine whether a cryogen level in the microscope cryogen holder has reached a threshold level; and
in response to determining that the cryogen level in the microscope cryogen holder has reached the threshold level, cause the valve control mechanism to close the at least one control valve of the delivery channel.

14. A cryogen refilling system for a microscope cryogen holder, comprising:
a reservoir assembly for holding cryogen;
a delivery channel in fluid communication with the reservoir assembly for delivering cryogen from the reservoir assembly to a microscope cryogen holder, wherein the delivery channel comprises at least one control valve;
a sensor-lid assembly comprising a sensor assembly configured to detect sensor data corresponding to a level of cryogen in the microscope cryogen holder, wherein the sensor assembly is configured to have a reentrant tube design; and
a controller, wherein the controller comprises:
a processor in communication with the sensor assembly, and
a computer-readable medium containing programming instructions that are configured to, when executed by the processor, cause the processor to:
periodically, cause a valve control mechanism to open the at least one control valve of the delivery channel to deliver cryogen to the microscope cryogen holder,
receive sensor data from the sensor assembly,
analyze the sensor data to determine whether cryogen level in the microscope cryogen holder has reached a threshold level, and
in response to determining that the cryogen level in the microscope cryogen holder has reached the threshold level, cause the valve control mechanism to close the at least one control valve of the delivery channel.

15. A cryogen refilling system for a microscope cryogen holder, comprising:
a reservoir assembly for holding cryogen;

a delivery channel in fluid communication with the reservoir assembly for delivering cryogen from the reservoir assembly to a microscope cryogen holder, wherein the delivery channel comprises at least one control valve;

a sensor-lid assembly comprising a sensor assembly configured to detect sensor data corresponding to a level of cryogen in the microscope cryogen holder, wherein the sensor assembly is configured to have a reentrant tube design; and a controller, wherein the controller comprises:
  a processor in communication with the sensor assembly, and
  a computer-readable medium containing programming instructions that are configured to, when executed by the processor, cause the processor to:
    receive sensor data from the sensor assembly,
    analyze the sensor data to determine whether the microscope cryogen holder requires refilling, and
    in response to determining that the microscope cryogen holder requires refilling, cause a valve control mechanism to open the at least one control valve of the delivery channel.

16. The cryogen refilling system of claim 15, wherein the sensor assembly comprises:
  a probe element comprising a first end and a second end, wherein:
    the first end of the probe element is in contact with liquid cryogen in the microscope cryogen holder when the microscope cryogen holder does not require refilling, and
    a temperature of the second end the probe element changes when the first end is in contact with liquid cryogen in the microscope cryogen holder compared to when the first end is not in contact with liquid cryogen; and
  a sensor element configured to collect temperature data corresponding to a temperature of the second end and transmit the temperature data to the processor.

17. The cryogen refilling system of claim 16, wherein the programming instructions that are configured to, when executed by the processor, cause the processor to analyze the temperature data to determine whether the microscope cryogen holder requires refilling, further comprise instructions to determine whether the temperature of the second end is above a threshold temperature.

18. The cryogen refilling system of claim 17, wherein the threshold temperature is selected from the group comprising: about 20° C. to about −100° C., about 10° C. to about −90° C., about 0° C. to about −80° C., about −10° C. to about −70° C., about −20° C. to about −60° C., about −30° C. to about −50° C., about 20° C., about 10° C., about 0° C. about −10° C., about −20° C., about −30° C., about −40° C., about −50° C., about −60° C., about −70° C., about −80° C., about −90° C., about −100° C.

19. The cryogen refilling system of claim 15, wherein the sensor-lid assembly further comprises a lid assembly configured to be mounted over an opening of the microscope cryogen holder.

20. The cryogen refilling system of claim 19, wherein the lid assembly comprises:
  a first opening configured to receive the sensor assembly; and
  a second opening configured to receive a delivery nozzle, wherein the delivery nozzle is in fluid communication with the delivery channel.

21. The cryogen refilling system of claim 15, further comprising a support frame, wherein:
  the support frame comprises an arm segment and a vertical segment; and
  the reservoir assembly is mounted on the arm segment via a sliding unit.

22. The cryogen refilling system of claim 21, wherein the sliding unit is configured to move the reservoir assembly along an axis parallel to a length of the arm segment.

23. The cryogen refilling system of claim 15, further comprising programming instructions that are configured to, when executed by the processor, cause the processor to, in response to determining that the microscope cryogen holder requires refilling, cause movement of at least one component of the cryogen refilling system such that the reservoir assembly is positioned to supply liquid cryogen to the microscope cryogen holder, before causing the valve control mechanism to open the at least one control valve of the delivery channel.

24. The cryogen refilling system of claim 15, wherein the reservoir assembly is configured to supply cryogen to the microscope cryogen holder using one or more of the following: gravity feeding, an external pump, or pressure feeding.

25. The cryogen refilling system of claim 15, wherein the reservoir assembly is configured to hold about 5 litres to about 25 litres of liquid cryogen.

26. The cryogen refilling system of claim 15, wherein the sensor assembly comprises a sensor element configured to collect sensor data corresponding to a change in cryogen level of the microscope cryogen holder and transmit the sensor data to the processor.

27. The cryogen refilling system of claim 26, wherein the sensor element comprises an ultrasound sensor.

28. The cryogen refilling system of claim 15, further comprising programming instructions that are configured to, when executed by the processor, cause the processor to, after causing the valve control mechanism to open the at least one control valve of the delivery channel:
  analyze the sensor data to determine whether a cryogen level in the microscope cryogen holder has reached a threshold level; and
  in response to determining that the cryogen level in the microscope cryogen holder has reached the threshold level, cause the valve control mechanism to close the at least one control valve of the delivery channel.

29. A cryogen refilling system for a microscope cryogen holder, comprising:
  a reservoir assembly for holding cryogen;
  a delivery channel in fluid communication with the reservoir assembly for delivering cryogen from the reservoir assembly to a microscope cryogen holder, wherein the delivery channel comprises at least one control valve;
  a sensor-lid assembly comprising a sensor assembly configured to detect sensor data corresponding to a level of cryogen in the microscope cryogen holder;
  a support frame, wherein:
    the support frame comprises an arm segment and a vertical segment, and
    the reservoir assembly is mounted on the arm segment via a sliding unit configured to move the reservoir assembly along an axis parallel to a length of the arm segment; and
  a controller, wherein the controller comprises:
    a processor in communication with the sensor assembly, and a computer-readable medium containing programming instructions that are configured to, when executed by the processor, cause the processor to:
receive sensor data from the sensor assembly,
analyze the sensor data to determine whether the microscope cryogen holder requires refilling, and
in response to determining that the microscope cryogen holder requires refilling, cause a valve control mechanism to open the at least one control valve of the delivery channel.

30. The cryogen refilling system of claim 29, wherein the sensor assembly comprises:
a probe element comprising a first end and a second end, wherein:
the first end of the probe element is in contact with liquid cryogen in the microscope cryogen holder when the microscope cryogen holder does not require refilling, and
a temperature of the second end the probe element changes when the first end is in contact with liquid cryogen in the microscope cryogen holder compared to when the first end is not in contact with liquid cryogen; and
a sensor element configured to collect temperature data corresponding to a temperature of the second end and transmit the temperature data to the processor.

31. The cryogen refilling system of claim 30, wherein the programming instructions that are configured to, when executed by the processor, cause the processor to analyze the temperature data to determine whether the microscope cryogen holder requires refilling, further comprise instructions to determine whether the temperature of the second end is above a threshold temperature.

32. The cryogen refilling system of claim 31, wherein the threshold temperature is selected from the group comprising: about 20° C. to about −100° C., about 10° C. to about −90° C., about 0° C. to about −80° C., about −10° C. to about −70° C., about −20° C. to about −60° C., about −30° C. to about −50° C., about 20° C., about 10° C., about 0° C. about −10° C., about −20° C., about −30° C., about −40° C., about −50° C., about −60° C., about −70° C., about −80° C., about −90° C., about −100° C.

33. The cryogen refilling system of claim 29, wherein the sensor-lid assembly further comprises a lid assembly configured to be mounted over an opening of the microscope cryogen holder.

34. The cryogen refilling system of claim 33, wherein the lid assembly comprises:
a first opening configured to receive the sensor assembly; and
a second opening configured to receive a delivery nozzle, wherein the delivery nozzle is in fluid communication with the delivery channel.

35. The cryogen refilling system of claim 29, further comprising programming instructions that are configured to, when executed by the processor, cause the processor to, in response to determining that the microscope cryogen holder requires refilling, cause movement of at least one component of the cryogen refilling system such that the reservoir assembly is positioned to supply liquid cryogen to the microscope cryogen holder, before causing the valve control mechanism to open the at least one control valve of the delivery channel.

36. The cryogen refilling system of claim 29, wherein the reservoir assembly is configured to supply cryogen to the microscope cryogen holder using one or more of the following: gravity feeding, an external pump, or pressure feeding.

37. The cryogen refilling system of claim 29, wherein the reservoir assembly is configured to hold about 5 litres to about 25 litres of liquid cryogen.

38. The cryogen refilling system of claim 29, wherein the sensor assembly comprises a sensor element configured to collect sensor data corresponding to a change in cryogen level of the microscope cryogen holder and transmit the sensor data to the processor.

39. The cryogen refilling system of claim 38, wherein the sensor element comprises an ultrasound sensor.

40. The cryogen refilling system of claim 29, further comprising programming instructions that are configured to, when executed by the processor, cause the processor to, after causing the valve control mechanism to open the at least one control valve of the delivery channel:
analyze the sensor data to determine whether a cryogen level in the microscope cryogen holder has reached a threshold level; and
in response to determining that the cryogen level in the microscope cryogen holder has reached the threshold level, cause the valve control mechanism to close the at least one control valve of the delivery channel.

41. A cryogen refilling system for a microscope cryogen holder, comprising:
a reservoir assembly for holding cryogen;
a delivery channel in fluid communication with the reservoir assembly for delivering cryogen from the reservoir assembly to a microscope cryogen holder, wherein the delivery channel comprises at least one control valve;
a sensor-lid assembly comprising a sensor assembly configured to detect sensor data corresponding to a level of cryogen in the microscope cryogen holder; and
a controller, wherein the controller comprises:
a processor in communication with the sensor assembly, and
a computer-readable medium containing programming instructions that are configured to, when executed by the processor, cause the processor to:
receive sensor data from the sensor assembly,
analyze the sensor data to determine whether the microscope cryogen holder requires refilling, and
in response to determining that the microscope cryogen holder requires refilling:
cause movement of at least one component of the cryogen refilling system such that the reservoir assembly is positioned to supply liquid cryogen to the microscope cryogen holder, and
upon positioning of the reservoir assembly, cause a valve control mechanism to open the at least one control valve of the delivery channel.

42. The cryogen refilling system of claim 41, wherein the sensor assembly comprises:
a probe element comprising a first end and a second end, wherein:
the first end of the probe element is in contact with liquid cryogen in the microscope cryogen holder when the microscope cryogen holder does not require refilling, and
a temperature of the second end the probe element changes when the first end is in contact with liquid cryogen in the microscope cryogen holder compared to when the first end is not in contact with liquid cryogen; and a sensor element configured to collect temperature data corresponding to a temperature of the second end and transmit the temperature data to the processor.

43. The cryogen refilling system of claim 42, wherein the programming instructions that are configured to, when executed by the processor, cause the processor to analyze the temperature data to determine whether the microscope cryogen holder requires refilling, further comprise instructions to determine whether the temperature of the second end is above a threshold temperature.

44. The cryogen refilling system of claim 43, wherein the threshold temperature is selected from the group comprising: about 20° C. to about −100° C., about 10° C. to about −90° C., about 0° C. to about −80° C., about −10° C. to about −70° C., about −20° C. to about −60° C., about −30° C. to about −50° C., about 20° C., about 10° C., about 0° C. about −10° C., about −20° C., about −30° C., about −40° C., about −50° C., about −60° C., about −70° C., about −80° C., about −90° C., about −100° C.

45. The cryogen refilling system of claim 41, wherein the sensor-lid assembly further comprises a lid assembly configured to be mounted over an opening of the microscope cryogen holder.

46. The cryogen refilling system of claim 45, wherein the lid assembly comprises:
a first opening configured to receive the sensor assembly; and
a second opening configured to receive a delivery nozzle, wherein the delivery nozzle is in fluid communication with the delivery channel.

47. The cryogen refilling system of claim 41, further comprising programming instructions that are configured to, when executed by the processor, cause the processor to, in response to determining that the microscope cryogen holder requires refilling, cause movement of at least one component of the cryogen refilling system such that the reservoir assembly is positioned to supply liquid cryogen to the microscope cryogen holder, before causing the valve control mechanism to open the at least one control valve of the delivery channel.

48. The cryogen refilling system of claim 41, wherein the reservoir assembly is configured to supply cryogen to the microscope cryogen holder using one or more of the following: gravity feeding, an external pump, or pressure feeding.

49. The cryogen refilling system of claim 41, wherein the reservoir assembly is configured to hold about 5 litres to about 25 litres of liquid cryogen.

50. The cryogen refilling system of claim 49, wherein the sensor assembly comprises a sensor element configured to collect sensor data corresponding to a change in cryogen level of the microscope cryogen holder and transmit the sensor data to the processor.

51. The cryogen refilling system of claim 50, wherein the sensor element comprises an ultrasound sensor.

52. The cryogen refilling system of claim 41, further comprising programming instructions that are configured to, when executed by the processor, cause the processor to, after causing the valve control mechanism to open the at least one control valve of the delivery channel:
analyze the sensor data to determine whether a cryogen level in the microscope cryogen holder has reached a threshold level; and
in response to determining that the cryogen level in the microscope cryogen holder has reached the threshold level, cause the valve control mechanism to close the at least one control valve of the delivery channel.

* * * * *